United States Patent
Prakash et al.

(10) Patent No.: US 6,423,864 B1
(45) Date of Patent: Jul. 23, 2002

(54) PURIFICATION OF N-[N-(3,3-DIMETHYLBUTYL)-L-α-ASPARTYL]-L-PHENYLALANINE 1-METHYL ESTER VIA CRYSTALLIZATION

(75) Inventors: Indra Prakash, Hoffman Estates; Christine M. V. Moore, Mount Prospect; Kurt Wachholder, Elgin, all of IL (US)

(73) Assignee: The NutraSweet Company, Chicago, IL (US)

( * ) Notice: Subject to any disclaimer, the term of this patent is extended or adjusted under 35 U.S.C. 154(b) by 0 days.

(21) Appl. No.: 09/448,671

(22) Filed: Nov. 24, 1999

Related U.S. Application Data

(60) Provisional application No. 60/110,000, filed on Nov. 25, 1998.

(51) Int. Cl.[7] .............................................. C07C 229/00
(52) U.S. Cl. .......................................... 560/41; 560/40
(58) Field of Search ...................................... 560/40, 41

(56) References Cited

U.S. PATENT DOCUMENTS

| | | | |
|---|---|---|---|
| 5,480,668 A | | 1/1996 | Nofre et al. ................. 426/548 |
| 5,502,238 A | * | 3/1996 | Rijkers et al. |
| 5,510,508 A | | 4/1996 | Claude et al. ................. 560/41 |
| 5,728,862 A | | 3/1998 | Prakash ........................ 560/40 |

* cited by examiner

*Primary Examiner*—Paul J. Killos
*Assistant Examiner*—Mahreen Chaudhry
(74) *Attorney, Agent, or Firm*—Fitzpatrick, Cella, Harper & Scinto; Jeffrey M Hoster

(57) ABSTRACT

N-[N-(3,3-dimethylbutyl)-L-α-aspartyl]-L-phenylalanine 1-methyl ester is crystallized in order to give highly pure product in high yield. In a preferred embodiment of the present invention, N-[N-(3,3-dimethylbutyl)-L-α-aspartyl]-L-phenylalanine 1-methyl ester is crystallized directly from an aqueous methanol reaction mixture.

38 Claims, No Drawings

PURIFICATION OF N-[N-(3,3-DIMETHYLBUTYL)-L-α-ASPARTYL]-L-PHENYLALANINE 1-METHYL ESTER VIA CRYSTALLIZATION

This application claims the benefit of U.S. Provisional Patent Application No. 60/110,000, filed Nov. 25, 1998.

BACKGROUND OF THE INVENTION

1. Field of the Invention

This invention relates to the purification of N-[N-(3,3-dimethylbutyl)-L-α-aspartyl]-L-phenylalanine 1-methyl ester (neotame) by crystallization to give highly pure product with high yields.

2. Related Background Art

N-[N-(3,3-dimethylbutyl)-L-α-aspartyl]-L-phenylalanine 1-methyl ester (neotame) is a high potency dipeptide sweetener (about 8000× sweeter than sucrose) that has the formula

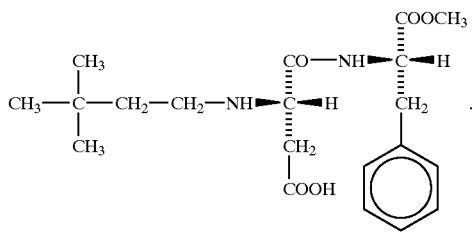

The chemical synthesis of neotame is disclosed in U.S. Pat. Nos. 5,480,668, 5,510,508 and 5,728,862, the disclosure of each of which is incorporated by reference herein. These chemical processes produce several troublesome impurities, including N,N-di(3,3-dimethylbutyl)-L-aspartyl-L-phenylalanine methyl ester (dialkylated aspartame), α-methyl hydrogen-3-(3,3-dimethylbutyl)-2-L-(2,2-dimethylpropyl)-5-oxo-α-L-(phenylmethyl)-1,4(L)-imidazolidine diacetate (dialkylated imidazolidinone), N-[N-(3,3-dimethylbutyl)-L-α-aspartyl]-L-phenylalanine (demethylated α- or β-neotame) and methyl ester of N-[N-(3,3-dimethylbutyl)-L-α-aspartyl]-L-phenylalanine 1-methyl ester (methylated α- or β-neotame). These impurities are represented respectively by the structural formulae:

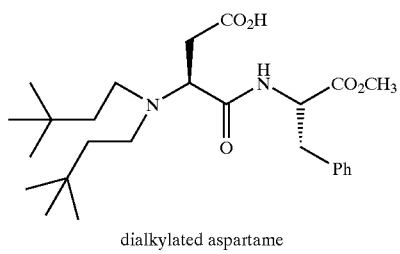
dialkylated aspartame

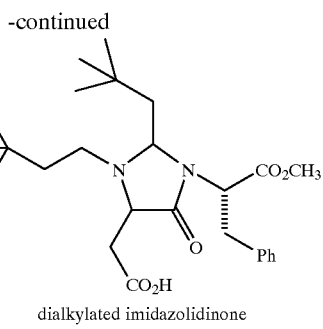
dialkylated imidazolidinone

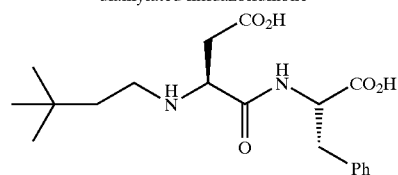
demethylated α-neotame

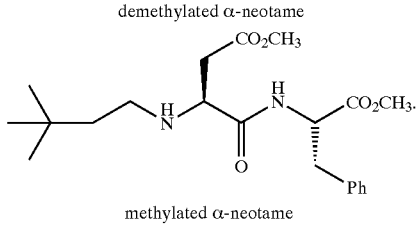
methylated α-neotame

U.S. Pat. No. 5,728,862 outlines a purification method by which neotame is precipitated out of an aqueous/organic solvent solution, wherein the aqueous/organic solvent solution has an amount of organic solvent of about 17% to about 30% by weight.

Since neotame is mainly employed in foods for human consumption, it is extremely important that neotame exist in a highly purified state. Thus, it is clear that there is a need to economically produce pure N-[N-(3,3-dimethylbutyl)-L-α-aspartyl]-L-phenylalanine 1-methyl ester.

SUMMARY OF THE INVENTION

The present invention is directed to a process of purifying N-[N-(3,3-dimethylbutyl)-L-α-aspartyl]-L-phenylalanine 1-methyl ester by crystallization from an aqueous solvent comprising the steps of: distilling organic solvent from an N-[N-(3,3-dimethylbutyl)-L-α-aspartyl]-L-phenylalanine 1-methyl ester reaction mixture; adding water to the reaction mixture to reach a desired organic solvent concentration; holding the reaction mixture for a time and at a temperature sufficient to hydrolyze dialkylated imidazolidinone to neotame and 3,3-dimethylbutyraldehyde; optionally, seeding the reaction mixture at an appropriate temperature and with an amount of N-[N-(3,3-dimethylbutyl)-L-α-aspartyl]-L-phenylalanine 1-methyl ester; and cooling the reaction mixture in order to crystallize N-[N-(3,3-dimethylbutyl)-L-α-aspartyl]-L-phenylalanine 1-methyl ester.

Another embodiment of the present invention is directed to a process of purifying N-[N-(3,3-dimethylbutyl)-L-α-aspartyl]-L-phenylalanine 1-methyl ester by crystallization from aqueous solvent comprising the steps of: adding water to an N-[N-(3,3-dimethylbutyl)-L-α-aspartyl]-L-phenylalanine 1-methyl ester reaction mixture; holding the reaction mixture for a time and at a temperature sufficient to hydrolyze dialkylated imidazolidinone to neotame and 3,3-dimethylbutyraldehyde; and distilling organic solvent in order to reach a desired organic solvent concentration and crystallize N-[N-(3,3-dimethylbutyl)-L-α-aspartyl]-L-phenylalanine 1-methyl ester.

Yet another embodiment of this invention is directed to a process for purifying N-[N-(3,3-dimethylbutyl)-L-α-aspartyl]-L-phenylalanine 1-methyl ester from an organic solvent comprising the steps of: dissolving N-[N-(3,3-dimethylbutyl)-L-α-aspartyl]-L-phenylalanine 1-methyl ester in an organic solvent; and crystallizing the purified N-[N-(3,3-dimethylbutyl)-L-α-aspartyl]-L-phenylalanine 1-methyl ester from the organic solvent. In this embodiment, the use of water is not required. Of course, the organic solvent may be, and preferably is, a mixture of organic solvents. For example, a first organic solvent may be added to dissolve N-[N-(3,3-dimethylbutyl)-L-α-aspartyl]-L-phenylalanine 1-methyl ester and a second organic solvent may be added to crystallize N-[N-(3,3-dimethylbutyl)-L-α-aspartyl]-L-phenylalanine 1-methyl ester.

A further embodiment of the invention is directed to a process for purifying N-[N-(3,3-dimethylbutyl)-L-α-aspartyl]-L-phenylalanine 1-methyl ester by simply mixing N-[N-(3,3-dimethylbutyl)-L-α-aspartyl]-L-phenylalanine 1-methyl ester with water and holding the mixture for a time and at a temperature sufficient to hydrolyze dialkylated imidazolidinone. The mixture may be completely aqueous, but preferably includes an organic solvent, which most preferably is methanol. The N-[N-(3,3-dimethylbutyl)-L-α-aspartyl]-L-phenylalanine 1-methyl ester may be isolated by any manner, e.g., crystallization or chromatographic separation, but most preferably by crystallization.

In preferred embodiments of the present invention, the organic solvent is selected from methanol, ethanol, isopropanol, butanol, ethyl acetate, methyl acetate, propyl acetate, acetone, tetrahydrofuran, acetonitrile, dichloromethane, toluene, cyclohexane, hexane, heptane, tertiary butyl methyl ether, diethyl ether, methyl ethyl ketone and mixtures thereof. In a particularly preferred embodiment of the present invention, the solvent is methanol.

DETAILED DESCRIPTION

According to the present invention, crystallization of N-[N-(3,3-dimethylbutyl)-L-α-aspartyl]-L-phenylalanine 1-methyl ester from the reaction mixture can be optimized in order to produce substantially pure N-[N-(3,3-dimethylbutyl)-L-α-aspartyl]-L-phenylalanine 1-methyl ester.

It has been found that N-[N-(3,3-dimethylbutyl)-L-α-aspartyl]-L-phenylalanine 1-methyl ester crystallization in aqueous methanol has a wide meta-stable crystallization zone which inhibits rapid nucleation. Seeding during crystallization can initiate a controlled crystal growth rate according to the present invention. Regardless, the same type of monohydrate crystals are obtained over a wide range of conditions (e.g., static, stirred, evaporative, slow cooling, and precipitation by non-polar solvent addition).

There are two methods by which the crystallization of the present invention can be performed. The first method is referred to as slow cooling. The second method is referred to as evaporative crystallization.

According to the first embodiment of the present invention, an organic solvent, such as methanol, is distilled from a reaction solution, and water is added. Then, the solution is held for a time and at a temperature sufficient to hydrolyze dialkylated imidazolidinone to a-neotame and 3,3-dimethylbutyraldehyde. The solution is optionally seeded. Finally, the solution is slowly cooled to crystallize N-[N-(3,3-dimethylbutyl)-L-α-aspartyl]-L-phenylalanine 1-methyl ester.

The reaction mixture, if seeded, is seeded in an amount from 0.0001%–10%, by weight of the N-[N-(3,3-dimethylbutyl)-L-α-aspartyl]-L-phenylalanine 1-methyl ester in the solution. Preferably this amount is from 0.1% to 1%. Most preferably this amount is from 0.1% to 0.5%. Seeding can occur between 5° C. and 300° C., preferably between 25° C.–30° C.

According to this method, the reaction mixture is generally cooled to a temperature of from about 5° C. to about 25° C. Crystallization preferably occurs by ramping the temperature after seeding to 4° C. over a time range of 0.5 to 12 hours.

Generally, lower seed and faster ramp gives larger crystals and slightly higher yields. Lesser seed also generally gives more uniformly sized crystals.

According to the second embodiment of the present invention, water is added to the reaction mixture, the solution is held for a time and at a temperature sufficient to hydrolyze dialkylated imidazolidinone to a-neotame and 3,3-dimethylbutyraldehyde and then an organic solvent, such as methanol, is distilled to the desired concentration. The N-[N-(3,3-dimethylbutyl)-L-α-aspartyl]-L-phenylalanine 1-methyl ester crystallizes during the distillation of the organic solvent. The solution may be optionally seeded as described above.

An additional embodiment of the present invention comprises adding water to the reaction mixture and then distilling an organic solvent, such as methanol, to the desired concentration. During this process, the dialkylated imidazolidinone is hydrolyzed to α-neotame and 3,3-dimethylbutyraldehyde. Again, the N-[N-(3,3-dimethylbutyl)-L-α-aspartyl]-L-phenylalanine 1-methyl ester crystallizes during the distillation of the organic solvent, and the solution may be optionally seeded as described above.

Additional embodiments of the present invention include purifying N-[N-(3,3-dimethylbutyl)-L-α-aspartyl]-L-phenylalanine 1-methyl ester by mixing it with water or with water and an organic solvent and holding the solution to hydrolyze dialkylated imidazolidinone to α-neotame and 3,3-dimethylbutyraldehyde.

As noted previously, methanol is the preferred organic solvent. According to the present invention, crystals grow satisfactorily from seeds in both 15% and 35% methanol solutions, with higher methanol concentrations requiring a lower temperature for crystal growth to accelerate. It should also be noted that higher methanol concentration during crystallization at lower temperatures results in higher purity neotame in high yield.

In additional embodiments of the present invention, organic solvents other than methanol may be used to crystallize N-[N-(3,3-dimethylbutyl)-L-α-aspartyl]-L-phenylalanine 1-methyl ester. Such alternate organic solvents include, without limitation, ethanol, isopropanol, butanol, ethyl acetate, methyl acetate, propyl acetate, acetone, tetrahydrofuran, acetonitrile, dichloromethane, toluene, cyclohexane, hexane, heptane, tertiary butyl methyl ether, diethyl ether, methyl ethyl ketone and mixtures thereof.

According to the present invention, the desired solvent concentration is generally between 15–35% by weight.

In a preferred embodiment of the present invention, the desired solvent concentration is between 25–30% by weight.

Further, in accordance with the present invention, the reaction mixture is held in order to hydrolyze the dialkylated imidazolidinone to a-neotame and 3,3-dimethylbutyraldehyde. The reaction mixture is generally held for 2–20 hours at a temperature of 40° C.–45° C. In a preferred embodiment of the present invention, the reaction mixture is held for 4–9 hours.

The reaction mixture or the solution containing neotame may be unstirred or stirred during the crystallization processes of the present invention.

The product isolated from any of these crystallization methods is the same monohydrate, which may be dried to produce an anhydrous form. The monohydrate formation is independent of cooling ramp, seed amount, seeding temperature and final temperature.

The Examples which follow are intended as an illustration of certain preferred embodiments of the invention, and no limitation of the invention is implied.

EXAMPLE 1
Evaporative Crystallization

A hydrogenation mixture containing neotame (8.36%), aspartame (0.35%), methylated α-neotame (0.04%), dialkylated aspartame (0.07%) and dialkylated imidazolidinone (0.03%) was obtained and filtered.

To half of the filtrate (347.5 g) was added 231 g of water. The solution was heated to 40° C. for 12 hours to hydrolyze the imidazolidinone. methanol was removed under reduced pressure (30–100 torr) at 23–27° C. Pressure during the distillation ranged from 30–100 torr. A total of 299.38 g of distillate were collected. After approximately two-thirds of the total distillate had been collected, material began to crystallize in the flask. The methanol level was determined by GC to be 25.1% (wt). The slurry was cooled to 5° C. for 12 hours, then the solid was filtered. The filter cake was washed with cold (10° C.) water (2×34 ml). The wet solid was dried for 12 hours under house vacuum with a nitrogen purge to yield 20.48 9 of pure neotame. All isolated crystals were neotame monohydrate. The product contained a total of 0.41% (wt) of dialkylated aspartame, methylated neotame, and dialkylated imidazolidinone by HPLC.

EXAMPLE 2
Slow Cooling

The other half of the filtrate from Example 1 (347.0 g) was charged to a flask and methanol removed under reduced pressure (30–80 torr) at 5–15° C. A total of 247.42 g of distillate was collected. Water (169 g) was then added and the solution heated to 42° for 18 hours to hydrolyze the imidazolidinone. The solution was then cooled slowly. When the temperature reached 26° C., approximately 4 ml of the solution was removed and cooled to generate crystals. These crystals were then added back to the solution to seed it. After stirring at room temperature for 4 hours, the solution was cooled to 5° C. over 5 hours. After 12 hours at 5° C., the solid was filtered and washed with cold water (2×34 ml). The wet crystals were dried for 24 hours under house vacuum with a nitrogen purge. This afforded 17.98 g of pure neotame. All isolated crystals were neotame monohydrate. The product contained a total of 0.33% (wt) of dialkylated aspartame, methylated α-neotame, and dialkylated imidazolidinone by HPLC.

EXAMPLE 3

Five crystallizations of neotame were conducted with varied methanol, dialkylated aspartame impurity and neotame concentration. Each experiment used the same stock hydrogenation mixture containing neotame (8.36%), aspartame (0.35%), demethylated a-neotame (0.03%), dialkylated aspartame (0.07%) and dialkylated imidazolidinone (0.03%). Water, methanol and purified neotame and/or dialkylated aspartame were added to achieve the desired concentrations. All batches were heated to 40° C. to 50° C. to dissolve all solids and then cooled to 28° C. over 1 hour. At this point, batch 3A already contained solids; all other batches were seeded with 0.25 wt % neotame. The batches were then cooled to 4° C. over 1.5 hours and held for an additional 2 hours. The solids were filtered, washed with water and then dried overnight at 40° C. in a vacuum oven. All crystals were neotame monohydrate. The results show that increasing methanol concentration is more effective at removing dialkylated aspartame, whereas lower methanol and higher neotame concentrations give higher yields. The experimental results are shown in Table 1.

TABLE 1

| | Crystallization Results. | | | | |
|---|---|---|---|---|---|
| | neo-tame (g/L) | dial-kylated aspartame (g/L) | meth-anol* (wt %) | crystal-lization yeild (%) | final solids-neo-tame (%) | final solids-dialkylated aspartame (%) |
| 3A | 180 | 0.8 | 20 | 88.4 | 98.5 | 0.07 |
| 3B | 80 | 2.3 | 20 | 84.0 | 100.3 | 0.97 |
| 3C | 80 | 2.3 | 35 | 73.8 | 102.4 | 0.08 |
| 3D | 180 | 2.3 | 35 | 87.7 | 100.5 | 0.19 |
| 3E | 180 | 0.8 | 35 | 88.3 | 104.3 | 0.00 |

*% methanol in solvent

EXAMPLE 4

In the following experiments, the amount of seed was varied. N-[N-(3,3-dimethylbutyl)-L-α-aspartyl]-L-phenylalanine 1-methyl ester was crystallized from a stock hydrogenation mixture containing aspartame (0.58%), α-neotame (28.9%), and dialkylated aspartame (0.4%) in methanol. The solvent content was adjusted to provide 105 g/l neotame and 30% methanol. The experiments were repeated twice. Each of the experiments used the same stock hydrogenation mixture, a jacket cooling ramp of 40°–28° C. over 1 hour, seed, if any, at 28° C., cooling from 28°–40° C. over 8 hours, and holding for 4–9 hours at 50° C. pot temperature. Table 2 summarizes the experimental results.

TABLE 2

Crystallization Results Varying Seed Amount.

|   | neotame (g/l) | seed amount (% neotame) | methanol* (wt %) | step yield (%) | Final Solids Purity Assay | | | |
|---|---|---|---|---|---|---|---|---|
|   |   |   |   |   | neotame | dialkylated aspartame | aspartame | dialkylated imidazolidinone |
| 4A | 105 | 1% | 30% | 78.1% | 96.5% | 0.10% | 0.0% | 0.0% |
| 4B | 105 | 0.5% | 30% | 82.0% | 94.7% | 0.16% | 0.0% | 0.0% |
| 4C | 105 | 0.1% | 30% | 80.3% | 95.8% | 0.18% | 0.0% | 0.0% |
| 4D | 105 | 0% | 30% | 82.4% | 96.4% | 0.19% | 0.0% | 0.17% |
| 4E | 105 | 1% | 30% | 80.1% | 97.0% | 0.15% | 0.05% | 0.0% |
| 4F | 105 | 0.5% | 30% | 82.4% | 102.4% | 0.17% | 0.0% | 0.0% |
| 4G | 105 | 0.1% | 30% | 83.3% | 94.3% | 0.17% | 0.0% | 0.0% |
| 4H | 105 | 0% | 30% | 81.0% | 92.9% | 0.21% | 0.08% | 0.0% |

*wt % methanol in solvent not including non-volatiles

The results show a slight decrease in dialkylated aspartame levels with increased amount of seed for both data sets. In the first experimental set (4A–4D), dialkylated imidazolidinone is only present in the unseeded batch; no dialkylated imidazolidinone was seen in the second experimental set. In the unseeded experiment, the solution became extremely supersaturated with no crystals forming even after holding at 50° C. for 8 hours. Crystallization was rapidly induced by addition of a few grains of seed. All isolated crystals were neotame monohydrate.

EXAMPLE 5
Crystallization of N-[N-(3,3-dimethylbutyl)-L-α-aspartyl]-L-phenylalanine 1-methyl Ester from Ethyl Acetate/Hexane N-[N-(3,3-dimethylbutyl)-L-α-aspartyl]-L-phenylalanine 1-methyl ester monohydrate (100 mg, obtained from Example 1) was dissolved in 1 ml of ethyl acetate at room temperature. Hexane (2 ml) was added. The mixture was cooled to 4° C.–60° C. for 12–16 hours. The crystallized solid was filtered and dried under vacuum (25" Hg) at 35° C.–40° C. to give 85 mg of neotame monohydrate.

EXAMPLE 6
Crystallization with Slow Cooling and Hold to Hydrolyze Dialkylated Imidazolidinone A filtered hydrogenation mixture (820 g) containing 3.7 g aspartame, 56.7 g neotame, 0.58 g dialkylated aspartame, and 0.22 g dialkylated imidazolidinone was concentrated on a rotary evaporator under vacuum to obtain 197 g. The methanol and water content of the concentrate were adjusted to obtain 10 wt % neotame and 30% methanol (on a solvent basis). The solution was stirred at 40° C. for 7 hours and then analyzed by HPLC to reveal that dialkylated imidazolidinone had hydrolyzed to non-detectable levels. The solution was cooled from 40° C. to 30° C. over 1 hour, and then from 30° C. to 5° C. over 7.5 hours. When the temperature reached 23° C., 0.1 g neotame seed was added. A thick crystal solution quickly formed. After a temperature of 50° C. was obtained, the crystal solution was filtered and washed twice with 50 ml of cold deionized water. The crystals were dried under vacuum at room temperature for several days. The final product weighed 45.2 g, contained 0.1 g aspartame and no detectable dialkylated aspartame or dialkylated imidazolidinone. The product was neotame monohydrate.

EXAMPLE 7
Addition of Water Before Distillation of Methanol

A hydrogenation mixture containing neotame (9.85%), aspartame (0.35%), methylated α-neotame (0.03%), dialkylated aspartame (0.09%) and dialkylated imidazolidinone (0.03%) was obtained and filtered.

To the filtrate (586.34 g), 250 g of water was added. Methanol was removed under reduced pressure (80–100 torr) at 20–26° C. A total of 435.62 g of distillate was collected. The solution was held at room temperature for 16 hours to hydrolyze the imidazolidinone. Then water (164 g) was added. The methanol level was found to be 27.8% by GC. Crystallization proceeded by introduction of seed crystals (0.14 g of neotame) into the solution. The seeded solution was cooled from 25° to 5° C. in two hours. After holding at 5° C. for 30 minutes the solid was filtered and washed with cold water (45 ml). The solid was dried under house vacuum for 20 hours to provide 48.28 g of pure neotame. The product contained a total of 0.14% dialkylated aspartame, methylated α-neotame, and dialkylated imidazolidinone. All isolated crystals were neotame monohydrate.

EXAMPLE 8
Static Crystallization of Neotame

A hydrogenation mixture containing neotame (10.29%), aspartame (0.41%), methylated α-neotame (0.13%), dialkylated aspartame (0.10%) and dialkylated imidazolidinone (0.01%) was obtained and filtered.

To half of the filtrate (270.05 g), 125 g of water was added. Methanol was removed under reduced pressure (100–200 torr) at 20–30° C. Distillation was halted after 197.12 g had been collected. Water (40 g) was added and the solution was heated to 40° C. for two hours to hydrolyze the imidazolidinone. The methanol level was found to be 28.2% by GC. After cooling the solution to 25° C., crystallization was initiated by seeding with 0.07 g of neotame crystals. The solution was then cooled with no agitation to 5° C. over two hours. After holding at 5° C. for 12 hours, the crystal mass was broken up with a glass rod and filtered. The cake was washed with cold water (2×20 ml). The wet product was dried under house vacuum with a nitrogen purge for 18 hours to give 22.86 g of neotame. This purified neotame contained a total of 0.17% dialkylated aspartame, methylated a-neotame, and dialkylated imidazolidinone. All isolated crystals were neotame monohydrate.

EXAMPLE 9
Crystallization without Seeding

Water (125 g) was added to the other half of the filtrate from Example 8. Methanol was removed under reduced pressure (100–200 torr) at 20–30° C. A total of 166.06 g of distillate was collected. Water (50 g) was added and the solution was heated to 40° C. for two hours to hydrolyze the imidazolidinone. The solution was cooled rapidly to 25° C. Then the solution was cooled slowly from 25° C. to 5° C. over 2 hours. After holding for 12 hours at 5° C., the material was filtered and washed with cold water (2×20 ml). The wet cake was dried under house vacuum with nitrogen purge. This yielded 20.82 g of neotame. All isolated crystals were neotame monohydrate. The material contained a total of 0.21% dialkylated aspartame, methylated α-neotame, and dialkylated imidazolidinone.

EXAMPLE 10

A neotame reaction mixture, containing 11.18% neotame, 0.59% aspartame, 0.03% methylated α-neotame, 0.25% dialkylated aspartame and 0.03% dialkylated imidazolidinone, was filtered to remove the catalyst. The filtrate (714.2 g) was mixed with water (206.3 g) and part of the solution was charged to a distillation vessel. Methanol was distilled under vacuum from the solution over 7.5 hours. Fresh solution was added to the vessel as distillation reduced the volume of liquid. Distillation was stopped when neotame concentration in the solution reached 14.68%. The concentrated solution was heated to 40° C. and transferred to a crystallizer. Methanol (9.6 g) and water (321.8 g) were added to the solution to bring the neotame and methanol concentrations to 8.2% and 27.5%, respectively. A specific hold period to hydrolyze the imidazolidinone was unnecessary due to the extended distillation time. The solution was cooled from 40° C. to 25° C. over 3 hours. At 25° C. the solution was seeded with neotame crystals (0.05 g). The seeded solution was further cooled to 7° C. over 16.5 hours. The crystallized solid was filtered, washed with cold water, and dried at 40° C. under house vacuum to yield 60.0 g of neotame. The dry product contained a total of 0.24% aspartame, methylated a-neotame, dialkylated aspartame and dialkylated imidazolidinone by HPLC.

EXAMPLE 11

Neotame (2 g obtained from Example 1) was dissolved in 18 g acetone at room temperature. Heptane (38.3 g) was added slowly until the solution turned cloudy. An additional 4 g of heptane was added, and the solution stirred for 1 hour. All solvents used were commercial grade. The solids were vacuum filtered and dried. The solids were determined to be monohydrate neotame by powder x-ray diffraction with a water content of 4.5% by TGA.

EXAMPLE 12

Neotame (3 g obtained from Example 1) was dissolved in 18 g dichloromethane. Heptane (27.6 g) was added to give a cloudy solution, at which time an additional 5.3 g of heptane was added. The mixture was stirred for 1 additional hour, filtered and dried. All solvents used were commercial grade. The solids were determined to be monohydrate neotame by powder x-ray diffraction with a water content of 4.4% by TGA.

Other variations and modifications of this invention will be obvious to those skilled in this art. This invention is not to be limited except as set forth in the following claims.

What is claimed is:

1. A process of purifying N-[N-(3,3-dimethylbutyl)-L-α-aspartyl]-L-phenylalanine 1-methyl ester by crystallization comprising the steps of:

(a) distilling organic solvent from an N-[N-(3,3-dimethylbutyl)-L-α-aspartyl]-L-phenylalanine 1-methyl ester reaction mixture;

(b) adding water to the reaction mixture to reach a solvent concentration of between 15% to 35% by weight;

(c) holding the reaction mixture for a time of 2 to 20 hours at between 40° C. to 45° C.;

(d) seeding the reaction mixture at a temperature between 30° C. to 5° C. with an amount of N-[N-(3,3-dimethylbutyl)-L-α-aspartyl]-L-phenylalanine 1-methyl ester from 0.0001% to 10% by weight based on the amount of N-[N-(3,3-dimethylbutyl)-L-α-aspartyl]-L-phenylalanine 1-methyl ester in the reaction mixture; and (e) cooling the reaction mixture to a temperature of about 4° C. over 0.5 hours to 12 hours in order to crystallize N-[N-(3,3-dimethylbutyl)-L-α-aspartyl]-L-phenylalanine 1-methyl ester.

2. The process according to claim 1, wherein the organic solvent is selected from the group consisting of methanol, ethanol, isopropanol, butanol, ethyl acetate, methyl acetate, propyl acetate, acetone, tetrahydrofuran, acetonitrile, dichloromethane, toluene, cyclohexane, hexane, heptane, tertiary butyl methyl ether, diethyl ether and mixtures thereof.

3. The process according to claim 2, wherein the organic solvent is methanol.

4. The process according to claim 1, wherein the solvent concentration in step (b) is from 25% to 30% by weight.

5. The process according to claim 1, wherein the reaction mixture in step (c) is held for 4 to 9 hours.

6. The process according to claim 1, wherein the reaction mixture in step (d) is seeded at a temperature between 30° C. to 25° C.

7. The process according to claim 1, wherein the reaction mixture in step (d) is seeded with an amount of N-[N-(3,3-dimethylbutyl)-L-α-aspartyl]-L-phenylalanine 1-methyl ester from 0.01% to 1% by weight based on the amount of N-[N-(3,3-dimethylbutyl)-L-α-aspartyl]-L-phenylalanine 1-methyl ester present in the reaction mixture.

8. The process according to claim 1, wherein the reaction mixture in step (e) is stirred or unstirred.

9. The process according to claim 1, wherein the crystallized N-[N-(3,3-dimethylbutyl)-L-α-aspartyl]-L-phenylalanine 1-methyl ester is a monohydrate.

10. A process of purifying N-[N-(3,3-dimethylbutyl)-L-α-aspartyl]-L-phenylalanine 1-methyl ester by crystallization comprising the steps of:

(a) distilling organic solvent from an N-[N-(3,3-dimethylbutyl)-L-α-aspartyl]-L-phenylalanine 1-methyl ester reaction mixture;

(b) adding water to the reaction mixture to reach a solvent concentration of between 15% to 35% by weight;

(c) holding the reaction mixture for a time of 2 to 20 hours at between 40° C. to 45° C.; and (d) cooling the reaction mixture to a temperature of about 4° C. over 0.5 hours to 12 hours in order to crystallize N-[N-(3,3-dimethylbutyl)-L-α-aspartyl]-L-phenylalanine 1-methyl ester.

11. The process according to claim 10, wherein the organic solvent is selected from the group consisting of methanol, ethanol, isopropanol, butanol, ethyl acetate, methyl acetate, propyl acetate, acetone, tetrahydrofuran, acetonitrile, dichloromethane, toluene, cyclohexane, hexane, heptane, tertiary butyl methyl ether, diethyl ether and mixtures thereof.

12. The process according to claim 11, wherein the organic solvent is methanol.

13. The process according to claim 10, wherein the solvent concentration in step (b) is from 25% to 30% by weight.

14. The process according to claim 10, wherein the reaction mixture in step (c) is held for 4 to 9 hours.

15. The process according to claim 10, wherein the reaction mixture in step (d) is stirred or unstirred.

16. The process according to claim 10, wherein the crystallized N-[N-(3,3-dimethylbutyl)-L-α-aspartyl]-L-phenylalanine 1-methyl ester is a monohydrate.

17. A process of purifying N-[N-(3,3-dimethylbutyl)-L-α-aspartyl]-L-phenylalanine 1-methyl ester by crystallization comprising the steps of:
(a) adding water to an N-[N-(3,3-dimethylbutyl)-L-α-aspartyl]-L-phenylalanine 1-methyl ester reaction mixture;
(b) holding the reaction mixture for a time of 2 to 20 hours at between 40° C. to 45° C.;
(c) distilling organic solvent from the reaction mixture in order to reach a solvent concentration of between 15% to 35% by weight;
(d) seeding the reaction mixture at a temperature between 30° C. to 5° C. with an amount of N-[N-(3,3-dimethylbutyl)-L-α-aspartyl]-L-phenylalanine 1-methyl ester from 0.0001% to 10% by weight based on the amount of N-[N-(3,3-dimethylbutyl)-L-α-aspartyl]-L-phenylalanine 1-methyl ester in the reaction mixture; and
(e) cooling the reaction mixture to a temperature of about 4° C. over 0.5 hours to 12 hours in order to crystallize N-[N-(3,3-dimethylbutyl)-L-α-aspartyl]-L-phenylalanine 1-methyl ester.

18. The process according to claim 17, wherein the organic solvent is selected from the group consisting of methanol, ethanol, isopropanol, butanol, ethyl acetate, methyl acetate, propyl acetate, acetone, tetrahydrofuran, acetonitrile, dichloromethane, toluene, cyclohexane, hexane, heptane, tertiary butyl methyl ether, diethyl ether and mixtures thereof.

19. The process according to claim 18, wherein the organic solvent is methanol.

20. The process according to claim 17, wherein the solvent concentration in step (c) is from 25% to 30% by weight.

21. The process according to claim 17, wherein the reaction mixture in step (b) is held for 4 to 9 hours.

22. The process according to claim 17, wherein the reaction mixture in step (e) is stirred or unstirred.

23. The process according to claim 17, wherein the crystallized N-[N-(3,3-dimethylbutyl)-L-α-aspartyl]-L-phenylalanine 1-methyl ester is a monohydrate.

24. The process according to claim 17, wherein the reaction mixture in step (d) is seeded at a temperature between 30° C. and 25° C.

25. The process according to claim 17, wherein the reaction mixture in step (d) is seeded with an amount of N-[N-(3,3-dimethylbutyl)-L-α-aspartyl]-L-phenylalanine 1-methyl ester from 0.01% to 1% by weight based on the amount of N-[N-(3,3-dimethylbutyl)-L-α-aspartyl]-L-phenylalanine 1-methyl ester present in the reaction mixture.

26. A process of purifying N-[N-(3,3-dimethylbutyl)-L-α-aspartyl]-L-phenylalanine 1-methyl ester by crystallization comprising the steps of:
(a) mixing N-[N-(3,3-dimethylbutyl)-L-α-aspartyl]-L-phenylalanine 1-methyl ester with water and an organic solvent;
(b) holding the mixture for a time of 2 to 20 hours at between 40° C. to 45° C.; and
(c) cooling the mixture to a temperature of about 4° C. over 0.5 hours to 12 hours in order to crystallize N-[N-(3,3-dimethylbutyl)-L-α-aspartyl]-L-phenylalanine 1-methyl ester.

27. The process according to claim 26, wherein said organic solvent is selected from the group consisting of methanol, ethanol, isopropanol, butanol, ethyl acetate, methyl acetate, propyl acetate, acetone, tetrahydrofuran, acetonitrile, dichloromethane, toluene, cyclohexane, hexane, heptane, tertiary butyl methyl ether, diethyl ether and mixtures thereof.

28. The process according to claim 27, wherein said organic solvent is methanol.

29. The process according to claim 26, wherein the organic solvent concentration in step (a) is from 15% to 35% by weight.

30. The process according to claim 29, wherein the organic solvent concentration in step (a) is from 25% to 30% by weight.

31. The process according to claim 26, wherein the mixture in step (b) is held for 4 to 9 hours.

32. A process of purifying N-[N-(3,3-dimethylbutyl)-L-α-aspartyl]-L-phenylalanine 1-methyl ester by crystallization comprising the steps of:
(a) mixing N-[N-(3,3-dimethylbutyl)-L-α-aspartyl]-L-phenylalanine 1-methyl ester with water to form an aqueous mixture;
(b) holding the aqueous mixture for a time of 2 to 20 hours at between 40° C. to 45° C.;
(c) seeding the aqueous mixture at a temperature between 30° C. to 5° C. with an amount of N-[N-(3,3-dimethylbutyl)-L-α-aspartyl]-L-phenylalanine 1-methyl ester from 0.0001% to 10% by weight based on the amount of N-[N-(3,3-dimethylbutyl)-L-α-aspartyl]-L-phenylalanine 1-methyl ester in the aqueous mixture; and
(d) cooling the aqueous mixture to a temperature of about 4° C. over 0.5 hours to 12 hours in order to crystallize N-[N-(3,3-dimethylbutyl)-L-α-aspartyl]-L-phenylalanine 1-methyl ester.

33. The process according to claim 32, wherein the aqueous mixture in step (d) is stirred or unstirred.

34. The process according to claim 32, wherein the crystallized N-[N-(3,3-dimethylbutyl)-L-α-aspartyl]-L-phenylalanine 1-methyl ester is a monohydrate.

35. The process according to claim 32, wherein the aqueous mixture in step (c) is seeded at a temperature between 30° C. to 25° C.

36. The process according to claim 32, wherein the aqueous mixture in step (c) is seeded with an amount of N-[N-(3,3-dimethylbutyl)-L-α-aspartyl]-L-phenylalanine 1-methyl ester from 0.01% to 1% by weight based on the amount of N-[N-(3,3-dimethylbutyl)-L-α-aspartyl]-L-phenylalanine 1-methyl ester present in the aqueous mixture.

37. A process of purifying N-[N-(3,3-dimethylbutyl)-L-α-aspartyl]-L-phenylalanine 1-methyl ester by crystallization comprising the steps of:
(a) mixing N-[N-(3,3-dimethylbutyl)-L-α-aspartyl]-L-phenylalanine 1-methyl ester with water to form an aqueous mixture;
(b) holding the aqueous mixture for a time of 2 to 20 hours at between 40° C. to 45° C.; and
(c) cooling the aqueous mixture to a temperature of about 4° C. over 0.5 hours to 12 hours in order to crystallize N-[N-(3,3-dimethylbutyl)-L-α-aspartyl]-L-phenylalanine 1-methyl ester.

38. The process according to claim 37, wherein the aqueous mixture in step (b) is held for 4 to 9 hours.

* * * * *